(12) United States Patent
Morimoto et al.

(10) Patent No.: US 10,939,688 B2
(45) Date of Patent: Mar. 9, 2021

(54) XANTHAN GUM GRANULATED MATERIAL AND COMPOSITION FOR THICKENING USE

(71) Applicant: Matsutani Chemical Industry Co., Ltd., Itami (JP)

(72) Inventors: Tomonori Morimoto, Itami (JP); Masaki Gouro, Itami (JP); Tomokazu Okazaki, Itami (JP)

(73) Assignee: MATSUTANI CHEMICAL INDUSTRY CO., LTD., Itami (JP)

( * ) Notice: Subject to any disclaimer, the term of this patent is extended or adjusted under 35 U.S.C. 154(b) by 392 days.

(21) Appl. No.: 15/548,530

(22) PCT Filed: Jul. 21, 2015

(86) PCT No.: PCT/JP2015/070737
§ 371 (c)(1),
(2) Date: Aug. 3, 2017

(87) PCT Pub. No.: WO2016/129132
PCT Pub. Date: Aug. 18, 2016

(65) Prior Publication Data
US 2018/0020690 A1    Jan. 25, 2018

(30) Foreign Application Priority Data

Feb. 12, 2015  (JP) .............................. JP2015-025493

(51) Int. Cl.
| | | |
|---|---|---|
| A61K 47/36 | (2006.01) | |
| A23L 29/269 | (2016.01) | |
| A23F 3/16 | (2006.01) | |
| A23L 2/52 | (2006.01) | |
| A23L 33/00 | (2016.01) | |

(52) U.S. Cl.
CPC .................. *A23F 3/16* (2013.01); *A23L 2/52* (2013.01); *A23L 29/27* (2016.08); *A23L 33/40* (2016.08); *A61K 47/36* (2013.01); *A23V 2002/00* (2013.01)

(58) Field of Classification Search
None
See application file for complete search history.

(56) References Cited

U.S. PATENT DOCUMENTS 5,585,513 A * 12/1996 Matthews .............. A01N 47/06
                                                    560/60
2008/0220081 A1* 9/2008 Farhat ................. C08B 37/0033
                                                    424/500

FOREIGN PATENT DOCUMENTS

| JP | 2004-49225 A | | 2/2004 |
| JP | 2007006745 A | * | 1/2007 |
| JP | 2011021005 A | * | 2/2011 |
| JP | 2011-229440 A | | 11/2011 |
| JP | 2011-244809 A | | 12/2011 |
| JP | 2013-111035 A | | 6/2013 |
| WO | WO-2014/034176 A1 | | 3/2014 |

OTHER PUBLICATIONS

Bell, The Structure/Physical Property Relationships of a Model Water-Dispersible Granule, Pesticide Science. 1990, 29, pp. 467-473 (Year: 1990).*
Knowles, Chemistry and Technology of Agrochemical Formulations, Springer Science, 1998, p. 91 (Year: 1998).*
Takahiro Doki et al., "Granulating Conditions for Preparation of Thickening Agents and Homogeneity of Granules," Journal of the Society of Powder Technology, Japan, 2009, pp. 371-375, vol. 46, No. 5, including partial English translation.
International Search Report dated Oct. 13, 2015 issued in PCT/JP2015/070737 filed Jul. 21, 2015.
International Search Report/Written Opinion dated Oct. 13, 2015 issued in PCT/JP2015/070737 filed Jul. 21, 2015 [non-English language].
European Patent Office, Extended European Search Report for European Patent Application No. 15882006.8, dated Sep. 6, 2018.

* cited by examiner

*Primary Examiner* — Viren A Thakur
*Assistant Examiner* — Thanh H Nguyen
(74) *Attorney, Agent, or Firm* — Faegre Drinker Biddle & Reath LLP

(57) ABSTRACT

The use of a granulated xanthan gum comprising, relative to 100% by mass of the granulated xanthan gum: xanthan gum granules having a degree of hardness of 2 N or higher and lower than 8 N in an amount of 5% by mass or higher; and xanthan gum granules having a degree of hardness of 8 N or higher in an amount of 20% by mass or lower makes it possible to provide a granulated xanthan gum and a thickening composition comprising the granulated xanthan gum which undergo suppressed formation of unmixed lumps in a wide variety of water-containing foods such as water, teas, refreshing beverages, dairy beverages, soups, and thick liquid foods, even when the xanthan gum concentration is 50% by mass or higher.

10 Claims, No Drawings

XANTHAN GUM GRANULATED MATERIAL AND COMPOSITION FOR THICKENING USE

This application is the National Stage of International Application No. PCT/JP2015/070737, filed Jul. 21, 2015, and claims benefit of Japanese Application No. 2015-025493 filed on Feb. 12, 2015.

TECHNICAL FIELD

The present invention relates to a granulated xanthan gum useful for preparation of a thickening composition excellent in solubility and also to a thickening composition excellent in solubility. In particular, the present invention relates to a thickening composition which has a high thickening activity per unit mass and is excellent in solubility.

BACKGROUND ART

As the population is getting older nowadays, the number of people with mastication and swallowing disorders who have impaired abilities of chewing and swallowing food is increasing. When accidental aspiration of a water-containing food occurs in a person with mastication and swallowing disorders, the food enters the bronchi and may cause a severe disease such as pneumonia. Therefore, it is necessary to pay special attention to ingestion of low-viscosity foods such as tea, milk, juice, and soup.

For the people with mastication and swallowing disorders, many products of thickening compositions for increasing the viscosity of liquid foods, which are so called thickening agents or swallowing aids, have been developed and put on the market. Especially, thickening compositions have been recently required to not only be resistant to the formation of unmixed lumps ("DAMA" in Japanese) or large unmixed lumps ("MAMAKO" in Japanese) when dissolved in water-containing foods, but also have characteristics such as rapid dispersing and expression of viscosity, good flavor and taste, high transparency, and low production costs.

Patent Literature 1 discloses a food texture-modifying composition which changes the rheology of a liquid food, the composition comprising: xanthan gum; and a water-soluble dispersant, wherein the xanthan gum and the water-soluble dispersant are each granulated. In the disclosed invention, the granulated xanthan gum and the granulated water-soluble dispersant have to be granulated to have particle diameters in a specific range of 250 nm to 710 μm, and the dispersibility is poor when the xanthan gum concentration is 50% by mass or higher relative to the xanthan gum and the water-soluble dispersant. For these reasons and the like, it is difficult to use xanthan gum at a high concentration of 50% by mass or higher.

Patent Literature 2 discloses a thickening agent comprising: a secondary granulated material obtained by adding one or more excipients selected from dextrin, starch, and saccharides to a primary granulated material, followed by granulation, the primary granulated material being obtained by granulation using at least powdery xanthan gum as a raw material and having a bulk specific gravity of 0.45 g/ml or less. Patent Literature 2 also discloses that the most preferred granulation method is fluidized-bed granulation. Patent Literature 2 discloses that the use of the thickening agent of the invention can suppress the formation of unmixed lumps. However, the thickener of the invention exhibits insufficient suppression of the formation of unmixed lumps when the thickener contains xanthan gum at a high concentration, for example, when the xanthan gum concentration exceeds 50% by mass in the thickener.

Patent Literature 3 discloses a method for producing a granulated thickener, comprising the steps of: spraying a binder liquid onto a primary raw material containing a thickening polysaccharide to obtain a primary granulated material; and coating the primary granulated material with a dextrin in an amount of 85 parts by mass or higher relative to 100 parts by mass of the thickening polysaccharide. Patent Literature 3 discloses that the granulated thickener produced by the method of the invention is good in dispersibility, resistant to the formation of unmixed lumps, rapid in rise in viscosity, and high in equilibrium viscosity. However, since it is necessary to add the dextrin in an amount of 85 parts by mass or higher relative to 100 parts by mass of the thickening polysaccharide, the concentration of the thickening polysaccharide in the granulated thickening material has to be 54% by mass or lower.

Patent Literature 4 discloses a thickening composition having an improved dispersibility comprising: a starch degradation product containing a metal salt; and a thickening polysaccharide. No improvement in dispersibility is observed when the thickening composition of the invention is such that the content ratio of the metal salt-containing starch degradation product is smaller than that expressed by metal salt-containing starch degradation product:thickening polysaccharide=55:45 (mass ratio), and hence the limitation to which the concentration of the thickening polysaccharide in the thickening composition can be increased is 45% by mass.

In addition, Non Patent Literature 1 describes two-step granulation for obtaining a uniform thickening agent. In this two-step granulation, granules of a thickening polysaccharide alone are produced in primary granulation, and then granules as a finished product are produced in secondary granulation by again granulating the granules obtained in the primary granulation together with a dispersant such as dextrin.

According to a test in Non Patent Literature 1, the concentration of the thickening polysaccharide in the finished product is 31% as shown in Table 3, and Non Patent Literature 1 does not describe any thickening composition in which the concentration of the thickening polysaccharide is 50% or higher in the finished product.

The ratio of the starch degradation product to the thickening polysaccharide is relatively high in the conventional thickening composition, and the amount of the thickening composition required to be added to a food for which a thickener is necessary to obtain a thickening effect is two times or more the amount in the case where the thickening polysaccharide is used alone. Accordingly, the possibility that this composition may affect the physical properties, the texture, or the taste of the food is undeniable.

CITATION LIST

Patent Literatures

Patent Literature

Patent Literature 1: Japanese Patent Application Publication No. 2004-049225
Patent Literature 2: Japanese Patent Application Publication No. 2011-244809
Patent Literature 3: Japanese Patent Application Publication No. 2011-229440
Patent Literature 4: Japanese Patent Application Publication No. 2013-111035

Non Patent Literature

Non Patent Literature 1: Journal of the Society of Powder Technology, Japan, 46(5), 2009, 371-375

SUMMARY OF INVENTION

Technical Problems

Accordingly, an object of the present invention is to provide a thickening composition comprising a large amount of a thickening polysaccharide. In other words, an object of the present invention is to provide a granulated xanthan gum for thickening composition which undergoes suppressed formation of unmixed lumps in a wide variety of water-containing foods such as water, teas, refreshing beverages, dairy beverages, soups, and thick liquid foods, even when the xanthan gum concentration in the thickening composition is 50% by mass or higher, as well as a thickening composition comprising the granulated xanthan gum and a method for producing the same. Moreover, another object of the present invention is to provide a granulated xanthan gum for preparing a thickening composition which undergoes suppressed formation of unmixed lumps even when the time for which the thickening composition is left to stand before stirring after addition to a food is long, and also to provide a thickening composition comprising the granulated xanthan gum and a method for producing the same.

Solution to Problems

The present inventors have conducted intensive study to achieve the above-described objects, and consequently found that, even when a thickening composition contains a large amount of xanthan gum, the formation of unmixed lumps is remarkably suppressed by adding, to the thickening composition, a granulated xanthan gum hardened to have a degree of hardness in a specific range.

Moreover, the present inventors have found that, even when the time for which a thickener is left to stand after addition to a food is long, the formation of unmixed lumps can be suppressed by adding, to the thickener, a granulated xanthan gum hardened to have a degree of hardness in a specific range. The present invention has been completed based on these findings.

The present invention provides the following.
[1] A granulated xanthan gum for thickening composition, comprising, relative to 100% by mass of the granulated xanthan gum:
xanthan gum granules having a degree of hardness of 2 N or higher and lower than 8 N in an amount of 5% by mass or higher; and
xanthan gum granules having a degree of hardness of 8 N or higher in an amount of 20% by mass or lower.
[2] A thickening composition comprising the granulated xanthan gum according to the above-described [1].
[3] The thickening composition according to the above-described [2], further comprising a water-soluble dispersant.
[4] The thickening composition according to the above-described [3], wherein
a mass ratio of the xanthan gum:the water-soluble dispersant in the thickening composition is 45:55 to 98:2.
[5] The thickening composition according to the above-described [3] or [4], wherein
the water-soluble dispersant is a metal salt-enclosing dextrin.
[6] The thickening composition according to any one of the above-described [3] to [5], which is obtained by granulating the granulated xanthan gum according to the above-described [1] and the water-soluble dispersant.
[7] The thickening composition according to any one of the above-described [2] to [6], which is used for a swallowing aid.
[8] A food comprising the thickening composition according to any one of the above-described [2] to [7].
[9] A method for producing a thickening composition, comprising the step of mixing or granulating a granulated xanthan gum and a water-soluble dispersant, the granulated xanthan gum having been prepared such that an amount of granules having a degree of hardness of 2 N or higher and lower than 8 N is 5% by mass or higher and an amount of granules having a degree of hardness of 8 N or higher is 20% by mass or lower, relative to 100% by mass of the granulated xanthan gum.

Advantageous Effects of Invention

The present invention makes it possible to provide a granulated xanthan gum for thickening composition which undergoes suppressed formation of unmixed lumps in a wide variety of water-containing foods such as water, teas, refreshing beverages, dairy beverages, soups, and thick liquid foods, even when the xanthan gum concentration in the thickening composition is as high as 50% by mass or higher, and also to provide a thickening composition comprising the granulated xanthan gum and a method for producing the same. The thickening composition of the present invention is excellent in dispersibility even when the xanthan gum concentration is high, and can impart a necessary viscosity to a food in a smaller amount than those in conventional cases. In addition, since the formation of unmixed lumps is suppressed even when the time for which the thickening composition is left to stand before stirring after addition to a food is long, it is not necessary to add the thickening composition to a food with stirring, or stir a food immediately after the thickening composition is added to the food as in conventional cases. Hence, the thickening composition is extremely easy to use.

DESCRIPTION OF EMBODIMENTS

The present invention includes a granulated xanthan gum for thickening composition, comprising: granules having a degree of hardness of 2 N or higher and lower than 8 N in an amount of 5% by mass or higher, and granules having a degree of hardness of 8 N or higher in an amount of 20% by mass or lower, a thickening composition comprising the granulated xanthan gum, and a method for producing the same.

In the present invention, a granulated xanthan gum refers to a mass of xanthan gum granules obtained by granulating a xanthan gum powder, and preferably a mass of xanthan gum granules obtained by adding a binder to a xanthan gum powder, followed by granulation, while a xanthan gum powder refers to a non-granulated xanthan gum powder.

In the present invention, the degree of hardness refers to a force (Unit: newton, N) necessary to crush a single granule. A granule is set on a creep meter (RE2-33005B, YAMADEN Co., Ltd.), and a load is gradually applied to the granule with a cylindrical rod. The granule is gradually distorted, and collapses at a certain load, where the displacement of the cylindrical rod sharply increases. The load required for the collapse of the granule is defined as the degree of hardness.

Specifically, first, a granulated xanthan gum is sorted with sieves (30 mesh, 42 mesh, 60 mesh, 83 mesh, 120 mesh, and 166 mesh). Ten xanthan gum granules present on the sieve of each mesh are randomly taken out, the degree of hardness of each of the granules is measured, and the average value of the degrees of hardness of the 10 granules is taken as the degree of hardness of the xanthan gum granules on the sieve.

Accordingly, in other words, the degree of hardness in the present invention means a value obtained by sorting a granulated xanthan gum with sieves (30 mesh, 42 mesh, 60 mesh, 83 mesh, 120 mesh, 166 mesh), and calculating the average degree of hardness of 10 xanthan gum granules present on the sieve of each mesh.

A method for measuring a granulated xanthan gum having a predetermined degree of hardness is as follows. Specifically, in the present invention, the ratio (% by mass) of xanthan gum granules on each sieve relative to the total mass is measured first, and then the average degree of hardness of 10 xanthan gum granules on each sieve is determined. Then, it is determined whether the ratio of xanthan gum granules having an average degree of hardness of 2 N or higher and lower than 8 N is 5% by mass or higher relative to the total mass and whether the ratio of xanthan gum granules having an average degree of hardness of 8 N or higher is 20% by mass or lower.

As the xanthan gum powder serving as a raw material of the granulated xanthan gum of the present invention, any commercially available xanthan gum powder can be used in general.

In the present invention, the granulated xanthan gum comprising: granules having a degree of hardness of 2 N or higher and lower than 8 N in an amount of 5% by mass or higher, and granules having a degree of hardness of 8 N or higher in an amount of 20% by mass or lower can be produced by using, for example, a tumbling fluidized-bed granulation apparatus or an extrusion granulation apparatus. Fluidized-bed granulation apparatuses, which have been conventionally used to produce thickeners for foods fail to produce the granulated xanthan gum comprising the hard granules of the present invention. A preferred manufacturing apparatus is a tumbling fluidized-bed granulation apparatus.

An example of the method for producing the granulated xanthan gum of the present invention is one using a tumbling fluidized-bed granulation apparatus in which a xanthan gum powder is introduced into the apparatus, and the xanthan gum powder is granulated (a primary granulated material is produced), while a binder liquid, which is prepared by dispersing or dissolving a binder in a suitable solvent, is being sprayed, with an impeller of the apparatus being rotated.

The rotation speed of the impeller may be adjusted in relation to the raw material used, the treatment time, and the like, and is set to, for example, 10 rpm to 600 rpm, preferably 100 rpm to 500 rpm, and more preferably 200 rpm to 400 rpm. In general, the hard xanthan gum granules of the present invention cannot be produced when the rotation seed of the impeller is low. Meanwhile, an excessively high rotation speed results in excessively hard xanthan gum granules.

In the present invention, an ordinary binder liquid can be used as the binder liquid used to produce the xanthan gum granules (primary granulated material). For example, water or an aqueous solution containing a thickening polysaccharide and/or dextrin can be used as the binder liquid.

For the production of the primary granulated material, it is preferable to use about 5 to 200 parts by mass of the binder liquid relative to 100 parts by mass of the xanthan gum powder.

When a thickening composition is prepared by using the granulated xanthan gum comprising: granules having a degree of hardness of 2 N or higher and lower than 8 N in an amount of 5% by mass or higher and granules having a degree of hardness of 8 N or higher in an amount of 20% by mass or lower obtained as described above, the formation of unmixed lumps is remarkably suppressed even in a case of a high-xanthan gum content thickening composition in which the xanthan gum concentration exceeds 50% by mass. In the present invention, the ratio of the xanthan gum granules having a degree of hardness of 2 N or higher and lower than 8 N is 5% by mass or higher, preferably 10% by mass or higher, more preferably 14% by mass or higher, and further preferably 19% by mass or higher, relative to 100% by mass of the granulated xanthan gum. In the present invention, the ratio of the granules having a degree of hardness of 8 N or higher in the granulated xanthan gum is 20% by mass or lower, preferably 10% by mass or lower, more preferably 4% by mass or lower, and further preferably 3% by mass or lower.

In the production of the granulated xanthan gum of the present invention, a thickener other than xanthan gum can be added, if necessary. Examples of the thickener include carrageenan, guar gum, gellan gum, agar, locust bean gum, tara gum, and glucomannan. In this case, the combined use of xanthan gum with a thickener other than xanthan gum is advantageous in, for example, that the thickening effect and the texture are improved. In addition, if necessary, the thickener other than xanthan gum may be mixed with the granulated xanthan gum of the present invention after production of the granulated xanthan gum.

The present invention includes a thickening composition comprising the above-described granulated xanthan gum. The thickening composition preferably comprises a water-soluble dispersant in addition to the above-described granulated xanthan gum. Examples of the water-soluble dispersant include lactose, glucose, and dextrin.

The thickening composition of the present invention preferably comprises a water-soluble dispersant in addition to the granulated xanthan gum comprising: granules having a degree of hardness of 2 N or higher and lower than 8 N in an amount of 5% by mass or higher, and granules having a degree of hardness of 8 N or higher in an amount of 20% by mass or lower. The thickening composition of the present invention can be prepared by mixing and/or granulating the granulated xanthan gum and the water-soluble dispersant. As a mixing apparatus, an ordinary mixing apparatus can be used, and examples thereof include mixing apparatuses such as a ribbon mixer and a nauta mixer. As a granulation apparatus, an ordinary granulation apparatus can be used, and is preferably a fluidized-bed granulation apparatus. The target thickening composition can be obtained also by using a tumbling fluidized-bed granulation apparatus without rotating the impeller.

In the present invention, for granulating the granulated xanthan gum comprising: granules having a degree of hardness of 2 N or higher and lower than 8 N in an amount of 5% by mass or higher, and granules having a degree of hardness of 8 N or higher in an amount of 20% by mass or lower and the water-soluble dispersant, the temperature of the hot air (intake air) is adjusted to 30 to 100° C., and preferably 70 to 100° C., and the temperature of the material during the granulation is adjusted to about 25 to 100° C., and preferably about 30 to 60° C. An excessively high temperature makes the granulation difficult, while an excessively low temperature results in low flowability.

Moreover, a binder liquid is preferably contained. As the binder liquid, it is possible to use water, as well as one or more selected from saccharides, dextrin, starch, gums, and CMC, or an aqueous solution or an aqueous suspension of any of them. In addition, it is also possible to use a thickening polysaccharide such as xanthan gum for the binder liquid. These can be used in the form of aqueous solutions. The spraying speed of the binder liquid varies depending on the type of the fluidized-bed apparatus, and, for example, the amount of the liquid can be generally about 0.01 to 2 L/minute. The drying may be conducted simultaneously with the fluidization treatment, or may be conducted in the next step separately from the fluidization treatment. When the drying is conducted simultaneously with the fluidization treatment, the drying can be conducted at 30 to 70° C., and preferably 40 to 60° C. Meanwhile, when the drying is conducted after the spraying process, the drying is preferably conducted at 70 to 100° C.

When the binder contains xanthan gum, the xanthan gum concentration may be calculated with the xanthan gum in the binder being included. In addition, when the binder contains a compound used as a dispersant, for example, dextrin, the dispersant concentration may be calculated with the compound being included.

When a secondary granulated material is produced, it is preferable to use the binder liquid in an amount of about 2.5 to 100 parts by mass relative to 100 parts by mass of the granulated xanthan gum.

In the present invention, the water-soluble dispersant is preferably dextrin.

The dextrin in the present invention refers to a starch hydrolysate obtained by hydrolysis of starch with an acid or an enzyme. The term dextrin also includes indigestible dextrins which are obtained by heating starch to which a trace amount of an acid is added, followed by hydrolysis with an enzyme. The dextrin is preferably digestible dextrin.

The DE in the present invention is an acronym of Dextrose Equivalent (glucose equivalent), which is an index widely used to express the degree of hydrolysis of a starch hydrolysate, and indicates the ratio of direct reducing sugars among solid components. In the present invention, the DE is a value analyzed by the Willstatter Schudel method.

The dextrin in the present invention preferably has a DE of 8 to 25. More preferably, the DE is 10 to 25, and further preferably 16 to 20. The dextrin may be in a powdery form or a granular form.

In addition, suppose a case where a metal salt (compound)-enclosing dextrin is used as the dextrin. In this case, the formation of unmixed lumps is suppressed even with a higher xanthan gum concentration than in a case where an ordinary dextrin is used. In the present invention, the "enclosure" of a metal salt in dextrin means that the metal salt is present in the dextrin in a homogenized state and refers to a non-crystalline (amorphous) state where no free metal salt crystals are present.

The thickening composition comprising the granulated xanthan gum and the metal salt-enclosing dextrin of the present invention undergoes remarkably suppressed formation of unmixed lumps even when the xanthan gum concentration in the thickening composition is as high as 50% by mass or higher.

The metal salt (compound) in the present invention is not particularly limited, as long as the metal salt is generally used for foods. From the viewpoints of excellent taste and the like, the metal salt is preferably an alkali metal salt or alkaline earth metal salt of an inorganic acid or organic acid. The metal salt compound is preferably one or more selected from calcium lactate, calcium acetate, calcium gluconate, calcium pantothenate, calcium ascorbate, magnesium sulfate, trisodium citrate, and tripotassium citrate. The metal salt compound is more preferably magnesium sulfate or calcium pantothenate.

In the present invention, the metal salt enclosed in the dextrin is prepared, for example, as follows. First, a dextrin and a metal salt are dissolved, mixed, and homogenized in water. Then, the solid content concentration is adjusted to 20 to 60% by mass, and preferably 30 to 55% by mass. Here, the dextrin may be prepared by hydrolysis of starch in a usual manner, or a commercially available one can be used as the dextrin. Considering that the dextrin is dried in a later step, it is preferable to use a liquid dextrin. The metal salt may be directly added to the aqueous dextrin solution, or a solution of the metal salt separately prepared at a high concentration in water may be added to the aqueous dextrin solution. After that, this mixture is dried to obtain a metal salt-enclosing dextrin. The drying can be conducted by a method such as spray drying, drum drying, vacuum drying, or freeze drying. Considering the efficiency, the cost, and the like, spray drying is preferable. Specifically, enclosure material can be prepared by preparing fine particles of the solution of the mixture of the dextrin with the metal salt by using an atomizer or a pressure nozzle, and then spraying the fine particles into a drying chamber in which the heated air temperature is adjusted to about 140 to 180° C., so that the outlet temperature can be about 80 to 100° C. For example, the concentration of the metal salt is preferably adjusted to be 45% by mass or lower relative to 100 parts by mass of the dextrin. If the concentration of the metal salt exceeds 45% by mass, the storage stability of the metal salt-enclosing dextrin and the recovery in the spray drying may greatly decrease in some cases.

In the present invention, the mass ratio of the xanthan gum comprising: granules having a degree of hardness of 2 N or higher and lower than 8 N in an amount of 5% by mass or higher, and granules having a degree of hardness of 8 N or higher in an amount of 20% by mass or lower to the water-soluble dispersant is such that the mass ratio of the xanthan gum:the water-soluble dispersant is preferably 45:55 to 75:25, more preferably 50:50 to 70:30, and further preferably 55:45 to 70:30, from the viewpoints of suppressed formation of unmixed lumps, rise in viscosity, and thickening effect. Here, when a water-soluble dispersant such as dextrin dissolved in water or the like is use as the binder for producing the granulated xanthan gum, the dextrin is contained in the granulated xanthan gum. Hence, the composition ratios of the xanthan gum and the dextrin are calculated with this point taken into consideration.

In the present invention, the mass ratio of the xanthan gum comprising: granules having a degree of hardness of 2 N or higher and lower than 8 N in an amount of 5% by mass or higher; and granules having a degree of hardness of 8 N or higher in an amount of 20% by mass or lower to the metal salt-enclosing dextrin is such that the ratio of the xanthan gum:the metal salt-enclosing dextrin is preferably 45:55 to 75:25, more preferably 50:50 to 98:2, further preferably 55:45 to 90:10, and most preferably 60:40 to 90:10, from the viewpoints of suppressed formation of unmixed lumps, rise in viscosity, and thickening effect.

The thus obtained thickening composition has a high thickening effect per unit mass, and a food can be made viscous by adding a small amount of the thickening composition. Hence, influences on the physical properties and texture of the food can be minimized, and the thickened food can be produced at low costs. In addition, even when the thickening composition of the present invention is left to stand before stirring for a certain period after the addition, the thickening composition is less likely to undergo the formation of unmixed lumps, and can be sufficiently dispersed. The amount of the thickening composition of the present invention blended in a food may be 0.5 to 3% by mass and preferably may be set within a range of 0.5 to 1.5% by mass according to the desired viscosity.

Foods for which the thickening composition of the present invention can be used include various water-containing foods. Examples thereof include water, tea beverages such as, green tea, and black tea; juices such as fruit juice-containing refreshing beverages, fruit juice beverages, and vegetable juice beverage; other beverages such as milk, dairy beverages, lactic acid bacteria beverages, carbonated beverages, isotonic beverages, functional beverages, vitamin supplement beverages, nutrients-supplement and balanced beverages, and powder beverages; alcoholic beverages such as wine, Japanese rice wines (Nihonshu in Japanese), Japanese spirits (Shochu in Japanese), whiskies, and cocktails; and foods such as soups, soybean paste soups, stews, curries, and porridges.

The thickening composition of the present invention is especially useful as a thickening composition which thickens foods for people with mastication and swallowing disorders.

In most cases, a thickened food for people with mastication and swallowing disorders is prepared at the site of nursing care by adding a thickening composition to a food such as water or tea, while the food is being stirred with a spoon. Accordingly, the use of the thickening composition comprising the granulated xanthan gum having improved dispersibility of the present invention makes it possible to reduce the work load on the caregiver. In addition, a thickening composition using the thickening composition of the present invention and having a high xanthan gum concentration makes it possible to reduce the amount of the thickening composition necessary to impart a target viscosity.

EXAMPLES

Hereinafter, the present invention is described in further detail based on Examples; however, the present invention is not limited to these Examples.
[1: Comparison with Conventional Products]
The dispersibility and the rise in viscosity were compared as follows between thickening compositions produced by using a granulated xanthan gum of the present invention and a conventional granulated xanthan gum.
[1-1. Preparation of Granulated Xanthan Gum of the Present Invention]
[Trial 1]
A granulated xanthan gum was produced by using 2.4 kg of water as a binder liquid relative to 3 kg of a xanthan gum powder (80 mesh pass) in a tumbling fluidized-bed granulator (flow coater equipped with rotor container FLO-05M, Freund Corporation). Specific conditions are as follows.
(Conditions of Trial 1):
  air temperature: 70° C., flow rate: 2.0 to 4.0 m³/minute,
  binder feed rate: 80 ml/minute, spray time: 30 minutes
  rotor rotation seed: 300 rpm

[1-2. Preparation of Granulated Xanthan Gums Using Conventional Flow Coater]
[Trial 2]
A granulated xanthan gum was produced by using 0.35 kg of water as a binder liquid relative to 3 kg of a xanthan gum powder (80 mesh pass) in a fluidized-bed granulator (flow coater FLO-5A, Freund Corporation). Specific conditions are as follows.
(Conditions of Trial 2):
  air temperature: 70° C., flow rate: 1.0 m³/minute,
  binder feed rate: 11.7 ml/minute, spray time: 30 minutes
[Trial 3]
A granulated xanthan gum was produced by employing the same conditions as in Trial 2, except that the spray time was changed to 1 hour.
[1-3. Method for Measuring Physical Properties of Granulated Xanthan Gums]
[Bulk Density]
A container having a capacity of 100 ml was filled with each granulated xanthan gum, and the granulated xanthan gum was leveled with the upper edges of the container. Then, the weight of the granules filling the container was measured to determine the bulk density.
[Particle Size Distribution]
Each granulated xanthan gum was sorted with the following sieves to measure the mass particle size distribution of the granulated xanthan gum.

| Mesh | Wire diameter (μm) | Aperture size (μm) |
| --- | --- | --- |
| 30 Mesh | 315 | 500 |
| 42 Mesh | 224 | 355 |
| 60 Mesh | 160 | 250 |
| 83 Mesh | 125 | 180 |
| 120 Mesh | 88 | 125 |
| 166 Mesh | 63 | 90 |

[Degree of Hardness]
From the xanthan gum granules present on the sieve of each mesh used for the particle size distribution measurement, 10 granules were randomly taken out, and the degree of hardness of each of the 10 granules was measured with a creep meter (RE2-33005B, YAMADEN Co., Ltd.). The loading rod used was a cylindrical rod having a diameter of 2.5 mm. The average value of the degrees of hardness of the 10 granules was regarded as the average degree of hardness of all the xanthan gum granules on the sieve, and the xanthan gum granules having the average degree of hardness were considered to be present at the percentage by mass determined by the particle size distribution measurement. Here, the granules passing through the sieve of 120 mesh may contain the non-granulated raw material powder, which deteriorates the precision of the measurement. Hence, the granules present on the sieves of 30 to 120 mesh were employed as the samples for measuring the degrees of hardness.
[1-4. Comparison of Physical Properties Among Granulated Xanthan Gums Produced]
Table 1 shows the measurement results of the mass distribution and the degree of hardness of the granulated xanthan gums produced in Trial 1, Trial 2, and Trial 3. As shown in Table 1, the bulk densities of all the granulated xanthan gums produced in Trials 1 to 3 were about 0.31 g/ml. However, the two were different in granule contents of specific degrees of hardness. No granules having numeric values of the degree of hardness were present in Trial 2 and Trial 3, whereas granules with a degree of hardness of 4.13

N was present at 3.2% by mass, and granules with a degree of hardness of 5.69 N was present at 10.5% by mass in Trial 1.

TABLE 1

|  |  | Trial 1 | Trial 2 | Trial 3 |
|---|---|---|---|---|
| Bulk density (g/ml) |  | 0.31 | 0.31 | 0.32 |
| Mass distribution (% by mass) | 30M on | 3.2 | 0 | 1.2 |
|  | 30M to 42M | 10.5 | 0 | 7.7 |
|  | 42M to 60M | 23.3 | 0 | 26.6 |
|  | 60M to 83M | 26.6 | 6.4 | 35.2 |
|  | 83M to 120M | 27.2 | 32.8 | 20.4 |
|  | 120M to 166M | 9.2 | 31.7 | 7.8 |
|  | 166M pass | 0.0 | 29.1 | 1.1 |
| Average value of degree of hardness (N) | 30M on | 4.13 | 0 | 0 |
|  | 30M to 42M | 5.69 | 0 | 0 |
|  | 42M to 60M | 0.0 | 0 | 0 |
|  | 60M to 83M | 0.0 | 0 | 0 |
|  | 83M to 120M | 0.0 | 0 | 0 |
| Content with Specific Degree of Hardness (% by mass) | 2N or higher to lower than 8N | 13.7 | 0 | 0 |
|  | 8N or higher | 0.0 | 0 | 0 |

[1-5. Preparation of Thickening Compositions]

Thickening compositions were produced as follows. Specifically, as shown in Table 2, the granulated xanthan gum of Trial 1, Trial 2, or Trial 3 was mixed with dextrin (TK-16, Matsutani Chemical Industry Co., Ltd.) at a ratio of xanthan gum:dextrin=70:30 (mass ratio), and secondary granulation was performed in a fluidized-bed granulator (flow coater FLO-5A, Freund Corporation) by using 300 g of an aqueous solution containing 0.2% by mass xanthan gum as a binder liquid relative to 2.0 kg of the mixture. Specific production conditions for the secondary granulation were as follows.
(Conditions for Secondary Granulation)
air temperature: 80° C., flow rate: 1.0 to 2.5 m³/minute
binder feed rate: 23 ml/minute, spray time: 13 minutes

TABLE 2

|  | Type of granulated xanthan gum | Concentration of xanthan gum (% by mass) | Dextrin |
|---|---|---|---|
| Example 1 | Trial 1 | 70 | TK-16 |
| Comp. Ex. 1 | Trial 2 | 70 | TK-16 |
| Comp. Ex. 2 | Trial 3 | 70 | TK-16 |

[1-6. Method for Evaluating Thickening Composition]
[Dispersibility—Testing Method]

In a 200 ml beaker, 100 g of ion-exchanged water is prepared at 20° ° C.±1° C. A thickening composition in an amount corresponding to 1 g of the thickening polysaccharide (xanthan gum) is added at once to the beaker, and the mixture is left to stand for 3 seconds, 5 seconds, or 10 seconds. After that, the mixture was stirred with a spatula at 200 rpm for 1 minute, and the state of unmixed lumps was visually observed.
[Evaluation of Dispersibility]

The state of the formation of unmixed lumps was converted to a numeric value, which was employed as the score of dispersibility. A higher score indicates a more preferred thickening composition with a more preferred dispersibility. Especially, a score of 4 points or higher under the condition where the mixture was left to stand for 5 seconds is preferable.

5: No unmixed lump
4: 1 to 3 small unmixed lumps
3: 4 to 10 small unmixed lumps
2: 10 or more small unmixed lumps
1: formation of a large unmixed lump(s) of 5 mm or larger
[Rise in Viscosity—Testing Method]

In a 200 ml beaker, 100 g of ion-exchanged water is prepared at 20° C.±1° C. While the ion-exchanged water was being stirred with a spatula at about 200 rpm, a thickening composition is added at once into the beaker in an amount corresponding to 1 g of the thickening polysaccharide (xanthan gum). The viscosity of the solution was measured with a BM-type viscometer (TOKIMEC) after a predetermined time has passed from the start of the dissolution.
[Evaluation of Rise in Viscosity]

The score of rise in viscosity based on the value of T was determined as follows, where T=[the value of viscosity after 3 minutes/the value of viscosity after 60 minutes]. A higher score indicates a more preferred thickening composition with a more preferred rise in viscosity. Especially, a score of 4 or higher is preferable.

5: $0.85 \leq X \leq 1$
4: $0.70 \leq X < 0.85$
3: $0.55 \leq X < 0.70$
2: $0.40 \leq X < 0.55$
1: $X < 0.40$

[1-7. Evaluation of Produced Thickener Compositions]

Each of the granulated xanthan gums of Trials 1 to 3 had a bulk density of about 0.31 g/ml. However, as shown in Table 3, the thickening composition of Example 1 using Trial 1, which was a granulated xanthan gum of the present invention, had an extremely good dispersibility, even though the xanthan gum concentration was as high as 70% by mass. Even under the harsh condition where the mixture was left to stand for 10 seconds after the thickening composition was added to the ion-exchanged water, the use of the thickening composition comprising the xanthan gum granules of Trial 1 did not result in formation of large unmixed lumps. On the other hand, each of the thickening compositions of Comparative Examples 1 and 2 using the granulated xanthan gums of Trials 2 and 3 produced with the conventional flow coater resulted in the formation of unmixed lumps even under the condition where the mixture was left to stand for 3 seconds. The results of the rise in viscosity of the thickening composition were good for both Example 1 and Comparative Example 1 (Table 4). A thickening composition with a high xanthan gum concentration was successfully prepared by using the granulated xanthan gum which had about the same density and/or particle size distribution, but which was different in degree of hardness.

Note that it was separately found that, in a case where the granulated xanthan gum of the present invention was used, the dispersibility was better even when the xanthan gum concentration was lower than 50% by mass in the thickening composition than in a case where a conventional granulated xanthan gum was used. In addition, the use of the conventional granulated xanthan gum resulted in an acceptable dispersibility at xanthan gum concentrations up to about 45% by mass. However, when the xanthan gum concentration was 50% by mass or higher, the dispersibility of the conventional granulated xanthan gum was poor, and the granulated xanthan gum became susceptible to the formation of unmixed lumps. This has demonstrated that the use of the granulated xanthan gum of the present invention is extremely effective for a thickening composition in which the xanthan gum concentration is 50% by mass or higher, preferably 55% by mass or higher, and more preferably 60% by mass or higher.

TABLE 3

| Example | Score of dispersibility evaluation | | |
|---|---|---|---|
| | Left at rest for 3 seconds | Left at rest for 5 seconds | Left at rest for 10 seconds |
| Example 1 | 5 | 4 | 3 |
| Comp. Ex. 1 | 1 | 1 | 1 |
| Comp. Ex. 2 | 2 | 1 | 1 |

TABLE 4

| Example | Viscosity measurement | | | Evaluation of rise in viscosity | |
|---|---|---|---|---|---|
| | After 3 minutes | After 30 minutes | After 60 minutes | 3 minutes/ 60 minutes | Score |
| Example 1 | 4950 | 6320 | 6250 | 0.79 | 4 |
| Comp. Ex. 1 | 4500 | 6100 | 6400 | 0.70 | 4 |
| Comp. Ex. 2 | 4300 | 6050 | 6350 | 0.67 | 3 |

[2. Detailed Examination of Degrees of Hardness of Granulated Xanthan Gums]

[2-1. Production of Granulated Xanthan Gums]

Granulated xanthan gums of Nos. S1 to S14 were produced by granulating the xanthan gum powder under the same conditions as in Trial 1, except for the treatment time, and sampling the granulated xanthan gum powder at predetermined intervals. The granulated xanthan gums were measured for the particle size distribution and the degree of hardness by the methods described in [1-3]. Table 5 shows the measurement results.

[2-2. Preparation of Thickening Compositions]

Thickening compositions were produced by using each of the granulated xanthan gums and dextrin (TK-16-AG, Matsutani Chemical Industry Co., Ltd.), which were mixed at a ratio of xanthan gum:dextrin=50:50 (mass ratio).

[2-3. Regarding Values of Degree of Hardness of Granulated Xanthan Gums]

With reference to Table 5, granules having specific degrees of hardness were extracted as granulated xanthan gums, and thickening compositions as described in [2-2] were produced. Specifically, by using granulated xanthan gums having an average degree of hardness of 1.38 N (extracted from 120 to 166 mesh of S12), 1.78 N (extracted from 83 to 120 mesh of S14), 2.13 N (extracted from 60 to 83 mesh of S14), 7.89 N (extracted from 30 to 42 mesh of S9), or 8.32 N (extracted from 60 to 83 mesh of S11), the thickening compositions as described in [2-2] were produced.

The above-described thickening compositions were subjected to the evaluation of dispersibility described in [1-6] (the leaving-at-rest time: 5 seconds). When the granulated xanthan gums having an average degree of hardness of 1.38 N or 1.78 N were used, many unmixed lumps were formed. On the other hand, when the granulated xanthan gums having an average degree of hardness of 2.13 N, 7.89 N, or 8.32 N were used, no unmixed lumps were formed even after leaving the mixture to stand for 5 seconds. In addition, the evaluation of rise in viscosity described in [1-6] was performed. When the granulated xanthan gum having an average degree of hardness of 8.32 N was used, the thickening composition resulted in a slow rise in viscosity (with a 3 minutes/60 minutes viscosity ratio of 0.65). Meanwhile, when the granulated xanthan gums having an average degree of hardness of 1.38 N, 1.78 N, 2.13 N, or 7.89 N were used, the thickening compositions resulted in excellent rise in viscosity (each having a 3 minutes/60 minutes viscosity ratio of 0.78 or higher). This indicates that, regarding the degree of hardness of xanthan gum granules in a granulated xanthan gum, the amount of granules having degrees of hardness of 2 N or higher to lower than 8 N is preferably large, and the amount of granules having degrees of hardness of 8 N or higher is preferably small.

TABLE 5

| Granulated xanthan gum No. | | S1 | S2 | S3 | S4 | S5 | S6 | S7 |
|---|---|---|---|---|---|---|---|---|
| Mass distribution (% by mass) | 30M on | 0.1 | 0.8 | 1.2 | 3.2 | 5.6 | 0.2 | 3.0 |
| | 30M to 42M | 1.1 | 3.7 | 8.9 | 10.5 | 14.0 | 8.5 | 8.9 |
| | 42M to 60M | 10.6 | 19.9 | 22.4 | 23.3 | 25.2 | 30.8 | 30.3 |
| | 60M to 83M | 31.7 | 30.5 | 29.5 | 26.6 | 26.3 | 38.1 | 38.4 |
| | 83M to 120M | 36.2 | 33.4 | 27.6 | 27.2 | 18.5 | 18.8 | 17.6 |
| | 120M to 166M | 13.3 | 11.7 | 10.4 | 9.2 | 6.6 | 3.0 | 1.0 |
| | 166M pass | 7.0 | 0.0 | 0.0 | 0.0 | 3.8 | 0.6 | 0.8 |
| Average value of degree of hardness (N) | 30M on | 4.57 | 4.22 | 5.61 | 4.13 | 4.71 | 5.76 | 8.20 |
| | 30M to 42M | 3.08 | 4.15 | 6.33 | 5.69 | 2.85 | 5.38 | 5.38 |
| | 42M to 60M | 0.0 | 0.0 | 0.0 | 0.0 | 0.0 | 3.45 | 3.45 |
| | 60M to 83M | 0.0 | 0.0 | 0.0 | 0.0 | 0.0 | 2.36 | 2.36 |
| | 83M to 120M | 0.0 | 0.0 | 0.0 | 0.0 | 0.0 | 0.0 | 0.0 |
| Content regarding specific degree of hardness (% by mass) | 2N or higher to lower than 8N | 1.2 | 4.5 | 10.1 | 13.7 | 19.6 | 77.6 | 77.6 |
| | 8N or higher | 0.0 | 0.0 | 0.0 | 0.0 | 0.0 | 0.0 | 3.0 |
| Granulated xanthan gum No. | | S8 | S9 | S10 | S11 | S12 | S13 | S14 |
| Mass distribution (% by mass) | 30M on | 0.9 | 5.0 | 8.2 | 4.6 | 7.7 | 8.2 | 27.8 |
| | 30M to 42M | 17.4 | 23.6 | 26.6 | 24.2 | 31.8 | 34.8 | 28.2 |
| | 42M to 60M | 42.9 | 36.8 | 35.7 | 36.6 | 34.5 | 36.7 | 23.2 |
| | 60M to 83M | 30.3 | 25.3 | 22.3 | 25.3 | 18.6 | 16.3 | 13.6 |
| | 83M to 120M | 7.2 | 8.3 | 6.4 | 8.1 | 6.1 | 3.6 | 5.5 |
| | 120M to 166M | 0.7 | 0.9 | 0.7 | 1.0 | 1.1 | 0.4 | 1.2 |
| | 166M pass | 0.6 | 0.1 | 0.1 | 0.2 | 0.2 | 0.0 | 0.5 |
| Average value of degree of hardness (N) | 30M on | 10.35 | 10.90 | 10.26 | 13.05 | 7.37 | 8.82 | 9.56 |
| | 30M to 42M | 8.93 | 7.89 | 6.13 | 11.48 | 10.25 | 8.40 | 4.77 |
| | 42M to 60M | 4.51 | 5.64 | 4.11 | 9.37 | 8.57 | 5.44 | 3.37 |
| | 60M to 83M | 4.00 | 7.78 | 5.83 | 8.32 | 4.14 | 5.97 | 2.13 |
| | 83M to 120M | 1.57 | 3.68 | 4.07 | 7.57 | 1.38 | 2.95 | 1.78 |

TABLE 5-continued

| Content regarding specific degree of hardness (% by mass) | 2N or higher to lower than 8N | 73.2 | 94.0 | 91.0 | 8.1 | 26.3 | 56.6 | 65.0 |
|---|---|---|---|---|---|---|---|---|
| | 8N or higher | 18.3 | 5.0 | 8.2 | 90.7 | 66.3 | 43.0 | 27.8 |

[2-4. Evaluation of Thickening Compositions Prepared by Using Granulated Xanthan Gums of S1 to S14]

Thickening compositions as described in [2-2] were produced by using the granulated xanthan gums of S1 to S15 as the granulated xanthan gum, and were subjected to the above-described evaluation of dispersibility and evaluation of rise in viscosity.

As shown in Table 6, thickening compositions each produced by using a granulated xanthan gum satisfying that the amount of granules having a degree of hardness of 2 N or higher and a degree of hardness of lower than 8 N was 5% by mass or higher, and that the amount of granules having a degree of hardness of 8 N or higher was 20% by mass or lower were excellent in dispersibility and excellent in rise in viscosity. In addition, thickening compositions produced by using the granulated xanthan gums (S5 to S7) in each of which the amount of granules having a degree of hardness of 2 N or higher and a degree of hardness of lower than 8 N was 19.6% by mass or higher, and the amount of granules having a degree of hardness of 8 N or higher was 3% by mass or lower were much better in both dispersibility and rise in viscosity.

Here, since the granules having an average degree of hardness of 2.13 N described in [2-3] were extracted from granules of 60 to 83 mesh, the particle diameters of the granules were in a range of 180 to 250 μm. The granulated xanthan gum of the present invention was excellent in dispersibility even when granules of 250 μm or smaller were used, in contrast to a case where xanthan gum granules of 250 μm or larger are used as mentioned in Patent Literature 1.

In addition, a thickening composition was prepared by mixing granules (average degree of hardness: 4.11 N) in the range of 42 to 60 mesh in the granulated xanthan gum of S9 with granules (average degree of hardness: 9.70 N) produced by extrusion granulation at 80:20 (mass ratio), followed by secondary granulation. Then, the thickening composition was evaluated for dispersibility and rise in viscosity in the same manner as described above. The dispersibility and rise in viscosity were good. In other words, it has been found that the thickening composition of the present invention can also be prepared by such a method.

TABLE 6

| | Granulated xanthan gum | Score of dispersibility evaluation | | Evaluation of rise in viscosity | |
|---|---|---|---|---|---|
| | | Left at rest for 3 seconds | Left at rest for 5 second | 3 minutes/ 60 minutes | Score |
| Comp. Ex. 3 | S1 | 2 | 2 | 1.00 | 5 |
| Comp. Ex. 4 | S2 | 3 | 2 | 0.99 | 5 |
| Example 2 | S3 | 5 | 4 | 0.97 | 5 |
| Example 3 | S4 | 5 | 4 | 0.96 | 5 |
| Example 4 | S5 | 5 | 5 | 0.92 | 5 |
| Example 5 | S6 | 5 | 5 | 1.00 | 5 |
| Example 6 | S7 | 5 | 5 | 0.91 | 5 |
| Example 7 | S8 | 5 | 5 | 0.79 | 4 |
| Example 8 | S9 | 5 | 5 | 0.70 | 4 |
| Example 9 | S10 | 5 | 5 | 0.75 | 4 |

TABLE 6-continued

| | Granulated xanthan gum | Score of dispersibility evaluation | | Evaluation of rise in viscosity | |
|---|---|---|---|---|---|
| | | Left at rest for 3 seconds | Left at rest for 5 second | 3 minutes/ 60 minutes | Score |
| Comp. Ex. 5 | S11 | 5 | 5 | 0.69 | 3 |
| Comp. Ex. 6 | S12 | 5 | 5 | 0.67 | 3 |
| Comp. Ex. 7 | S13 | 5 | 5 | 0.65 | 3 |
| Comp. Ex. 8 | s14 | 5 | 5 | 0.67 | 3 |

[3. Examination of Xanthan Gum Concentration]

[3-1. Production of Thickening Compositions]

As shown in Tables 7 and 8, thickening compositions were each produced by using the granulated xanthan gum of No. S3 or S5 and a dextrin at ratios of xanthan gum: dextrin=70:30 to 98:2 (mass ratio). The dextrins used were metal salt-enclosing dextrins with a DE of 18.

The metal salt-enclosing dextrins were each prepared by dissolving a metal salt in an aqueous solution which had been obtained by dissolving 100 g of dextrin in 300 g of ion-exchanged water such that the resultant metal salt concentration in the enclosure material was as shown in Table 7, and then drying the mixture using a spray-drying method or a drum-drying method.

TABLE 7

| | Xanthan gum concentration (% by mass) | Dextrin used | | | |
|---|---|---|---|---|---|
| | | Granulated xanthan gum used | Metal salt concentration (% by mass) | Drying method | Treatment method |
| Example 10 | 70 | S5 | 8.25 | Spray | Granulation |
| Example 11 | 80 | S5 | 17.00 | Spray | Granulation |
| Example 12 | 80 | S5 | 10.00 | Drum | Mixing |
| Example 13 | 90 | S5 | 49.50 | Spray | Granulation |
| Example 14 | 90 | S5 | 10.00 | Drum | Mixing |
| Example 15 | 95 | S5 | 10.00 | Drum | Mixing |
| Example 16 | 96 | S5 | 10.00 | Drum | Mixing |
| Example 17 | 98 | S5 | 20.00 | Drum | Mixing |
| Comp. Ex. 9 | 100 | S5 | — | — | — |

TABLE 8

| | Xanthan gum concentration (% by mass) | Dextrin used | | | |
|---|---|---|---|---|---|
| | | Granulated xanthan gum used | Metal salt concentration (% by mass) | Drying method | Treatment method |
| Example 18 | 70 | S3 | 8.25 | Spray | Granulation |
| Example 19 | 80 | S3 | 17.00 | Spray | Granulation |
| Example 20 | 80 | S3 | 10.00 | Drum | Mixing |
| Example 21 | 90 | S3 | 49.50 | Spray | Granulation |
| Example 22 | 90 | S3 | 10.00 | Drum | Mixing |
| Example 23 | 95 | S3 | 10.00 | Drum | Mixing |

[3-2. Evaluation of Thickening Compositions]

As shown in Tables 9 and 10, the thickening compositions in which the xanthan gum concentration was 70% by mass achieved good results in terms of both the dispersibility and the rise in viscosity. Although the thickening composition produced by using the ordinary dextrin was highly evaluated as shown in Example 1, the use of the metal salt-enclosing dextrin further improved the dispersibility to an extent that unmixed lumps were not formed even when the mixture was left to stand for 5 seconds after the thickening composition was added to the aqueous solution.

In addition, regarding the method for producing a metal salt-enclosing dextrin, both the spraying method and the drum method achieved favorable results. From the viewpoint that the amount of the metal salt can be reduced, the use of the metal salt-enclosing dextrin produced by the drum method achieved more preferred results.

The use of the granulated xanthan gum of the present invention enabled successful production of thickening compositions from which no unmixed lumps were formed. Specifically, when the metal salt-enclosing dextrin produced by the spray method was used, no unmixed lumps were formed even when the xanthan gum concentration in the thickening composition was 90% by mass. Meanwhile, when the metal salt-enclosing dextrin produced by the drum method was used, no unmixed lumps were formed even when the xanthan gum concentration in the thickening composition was 98% by mass. From the viewpoint that no unmixed lumps are formed even when a thickening composition is left to stand for 5 seconds after addition to an aqueous solution, the xanthan gum concentration in the thickening composition is preferably 90% by mass at the highest.

Note that when a dextrin not enclosing any metal salt is used as the dispersant, the xanthan gum concentration in the thickening composition is preferably 75% by mass at the highest from the viewpoint of rise in viscosity.

TABLE 9

| | Xanthan gum concentration % by mass | Score of dispersibility evaluation | | Evaluation of rise in viscosity | |
|---|---|---|---|---|---|
| | | Left at rest for 1 second | Left at rest for 5 seconds | 3 minutes/ 60 minutes | Score |
| Example 10 | 70 | 5 | 5 | 0.98 | 5 |
| Example 11 | 80 | 5 | 5 | 0.98 | 5 |
| Example 12 | 80 | 5 | 5 | 0.98 | 5 |
| Example 13 | 90 | 5 | 5 | 0.98 | 5 |
| Example 14 | 90 | 5 | 5 | 0.98 | 5 |
| Example 15 | 95 | 5 | 4 | 0.97 | 5 |
| Example 16 | 96 | 5 | 1 | 0.97 | 5 |
| Example 17 | 98 | 5 | 1 | 0.97 | 5 |
| Comp. Ex. 9 | 100 | 1 | 1 | 0.17 | 1 |

TABLE 10

| | Xanthan gum concentration % by mass | Score of dispersibility evaluation | | Evaluation of rise in viscosity | |
|---|---|---|---|---|---|
| | | Left at rest for 1 second | Left at rest for 5 seconds | 3 minutes/ 60 minutes | Score |
| Example 18 | 70 | 5 | 5 | 0.98 | 5 |
| Example 19 | 80 | 5 | 5 | 0.98 | 5 |
| Example 20 | 80 | 5 | 5 | 0.98 | 5 |
| Example 21 | 90 | 5 | 5 | 0.98 | 5 |
| Example 22 | 90 | 5 | 5 | 0.98 | 5 |
| Example 23 | 95 | 5 | 3 | 0.97 | 5 |

[4. Effect of Thickening Composition on Common Beverage]

Example 18 Tea

To 100 g of tea (trade name: "Oi Ocha", ITO EN, LTD.), 0.7 g of the thickening composition prepared in Example 10 was added, followed by stirring with a spatula. The thickening composition was immediately dispersed all over the liquid. No unmixed lumps were formed, and the expression of viscosity was also good. The addition in an amount of only 0.7 g provided a viscosity sufficient for tea for people with mastication and swallowing disorders.

Example 19 Refreshing Beverage

To 100 g of a refreshing beverage (trade name: "AQUARIUS," Coca-Cola (Japan) Company, Limited), 0.7 g of the thickening composition prepared in Example 10 was added, followed by stirring with a spatula. The thickening composition was immediately dispersed all over the liquid. No unmixed lumps were formed, and the expression of viscosity was good. The addition in an amount of only 0.7 g provided a viscosity sufficient for tea for people with mastication and swallowing disorders.

[5. Regarding Degree of Hardness of Granules in Thickening Compositions]

The degree of hardness of granules in the thickening composition of Example 1 was examined by the method described in [1-3]. The degree of hardness was very similar to the distribution of degree of hardness of the granules in the granulated xanthan gum (Trial 1) used for the preparation of the thickening composition. In addition, the degree of hardness of granules in the thickening composition of Comparative Example 2 was also examined. Although only a small fraction of the granules exhibited some degree of hardness, 99% by mass or higher of the granules had a degree of hardness of 0.

It has been found that the degree of hardness of the granules in the thickening composition of the present invention is similar to the degree of hardness of the granules in the granulated xanthan gum used.

The invention claimed is:

1. A granulated xanthan gum composition comprising, relative to 100% by mass of the granulated xanthan gum composition:
    (i) xanthan gum granules having a degree of hardness of 2 N or higher and lower than 8 N in an amount of 10% by mass or higher; and
    (ii) xanthan gum granules having a degree of hardness of 8 N or higher in an amount of 3% by mass or lower.

2. A thickening composition comprising the granulated xanthan gum composition according to claim 1.

3. The thickening composition according to claim 2, further comprising a water-soluble dispersant.

4. The thickening composition according to claim 3, wherein a mass ratio of the xanthan gum composition: the water-soluble dispersant in the thickening composition is 45:55 to 98:2.

5. The thickening composition according to claim 3, wherein the water-soluble dispersant is a metal salt-enclosing dextrin.

6. The thickening composition according to claim 3, which is obtained by granulating the granulated xanthan gum composition and the water-soluble dispersant.

7. A water-containing food comprising the thickening composition according to claim 2.

8. A method for producing a thickening composition, comprising the step of mixing or granulating a granulated xanthan gum composition and a water-soluble dispersant,
   wherein the granulated xanthan gum composition comprises (i) an amount of xanthan gum granules having a degree of hardness of 2 N or higher and lower than 8 N in an amount of 10% by mass or higher, and (ii) an amount of xanthan gum granules having a degree of hardness of 8 N or higher in an amount of 3% by mass or lower relative to 100% by mass of the granulated xanthan gum composition.

9. The thickening composition according to claim 3, further comprising a binder liquid.

10. A method of producing a water-containing food comprising mixing the thickening composition of claim 2 with a food to obtain the water-containing food.

* * * * *